United States Patent [19]

Carroll et al.

[11] Patent Number: 5,183,904

[45] Date of Patent: Feb. 2, 1993

[54] HINDERED LINKING AGENTS AND METHODS

[75] Inventors: Stephen F. Carroll, Walnut Creek, Calif.; Dane A. Goff, Menlo Park, both of Calif.

[73] Assignee: Xoma Corporation, Berkeley, Calif.

[21] Appl. No.: 796,048

[22] Filed: Nov. 20, 1991

Related U.S. Application Data

[60] Division of Ser. No. 454,576, Dec. 21, 1989, Pat. No. 5,093,475, which is a continuation-in-part of Ser. No. 288,586, Dec. 22, 1988, abandoned.

[51] Int. Cl.$^5$ ............................................. C07D 333/36
[52] U.S. Cl. .................................... 549/68; 549/13; 549/28; 549/54; 549/55; 549/57; 549/60; 549/63; 546/284
[58] Field of Search ................ 549/68, 69, 63, 60, 549/28, 13, 54, 55, 57; 546/284

[56] References Cited

U.S. PATENT DOCUMENTS

| | | | |
|---|---|---|---|
| 3,223,585 | 12/1965 | Addor | 549/68 |
| 3,317,562 | 5/1967 | Addor | 549/68 |
| 3,318,910 | 5/1967 | Addor | 549/6 |
| 3,755,364 | 8/1973 | Magee | 549/68 |
| 4,590,071 | 5/1986 | Scannon et al. | 424/85.41 |
| 4,880,935 | 11/1989 | Thorpe | 546/281 |
| 4,888,415 | 12/1989 | Lambert et al. | 530/341 |

FOREIGN PATENT DOCUMENTS 86-05098 9/1986 World Int. Prop. O.

OTHER PUBLICATIONS

P. Thorpe et al., *JNCI*, 79(55), pp. 1101–1112 (1987).
P. Thorpe et al., *Cancer Res.* 47, pp. 5924–5931 (1987).
S. Aizawa, et al., *Biochem, Biophys. Res. Commun.*, 75 (4) pp. 870–878 (1977).
T. King et al., *Biochemistry*, 17 (8), pp. 1499–1506 (1978).
N. Letuin et al., *J. Clin. Invest.* 77, pp. 977–984 (1986).
J. Lambert et al., *J. Biol. Chem.*, 260, pp. 12035–12041, (1985).
C. Scott et al., *JNCI*, 79 (5), pp. 1101–1112 (1978).
J. Carlsson et al., *Biochemical Journal 173*, pp. 723–737 (1978).
A. Alagon et al., *Biochemistry*, 19 4341–4345 (1980).
A. Blair et al., *J. Immunol. Methods*, 59, pp. 129–143 (1983).
Stoffel et al., *Hoppe-Seylen's Z. Physiol. Chem.*, 360, pp. 691–707 (1979).
E. J. Wawrzynczak et al., *Immunoconjugates," Antibody Conjugates in Radioimaging . . . " (G. W. Vogel, ed.), N.Y. Oxford Univ. Press, pp. 28–55 (1987).*
R. Jue, et al., *Biochemistry*, 17 (25), pp. 5399–5406 (1978).

*Primary Examiner*—Richard L. Raymond
*Assistant Examiner*—Mark W. Russell
*Attorney, Agent, or Firm*—Townsend and Townsend

[57] ABSTRACT

Novel compounds and methods for the formation of disulfide linkages are presented. The novel compounds employed are substituted 2-iminothiolane hydrohalide linking agents of the following formula (I):

$$\begin{array}{c} R_1 \\ R_2 \\ R_3 \\ R_4 \end{array} \begin{array}{c} S \\ \diagup \\ CH_2 \end{array} =NH_2^+ ; X^- \qquad (I)$$

wherein,

X is halogen;

$R_1$ is $COOR_5$; halogen; nitro; unsubstituted or halogenated $C_{1-8}$alkyl; unsubstituted or halogenated $C_{1-8}$alkoxy; unsubstituted or halogenated $C_{2-8}$alkenyl; unsubstituted or halogenated $C_{2-8}$alkynyl; unsubstituted $C_{3-8}$cycloalkyl; unsubstituted aryl; aryl substituted with 1 to 3 substituents selected from halogen, amino, unsubstituted or halogenated $C_{1-8}$alkyl, or unsubstituted or halogenated $C_{1-8}$alkoxy; unsubstituted heterocycle; or heterocycle substituted with 1 to 3 substituents selected from amino, halogen, unsubstituted or halogenated $C_{1-8}$alkyl, or unsubstituted or halogenated $C_{1-8}$alkoxy;

each of $R_2$, $R_3$ and $R_4$ is independently hydrogen or selected from the values of $R_1$; or $R_1$ and $R_2$ together form a $C_{2-5}$alkylene bridge, unsubstituted or substituted with one to five $C_{1-4}$alkyl groups; or $R_1$ or $R_2$ together with $R_3$ form a $C_{1-5}$alkylene bridge, unsubstituted or substituted with one to five $C_{1-4}$alkyl groups; and $R_5$ is hydrogen or $C_{1-8}$alkyl.

Also included in the invention are methods for covalently linking two species, which methods comprise reacting one or both of the two species with a crosslinking agent of the above formula (I) and mixing the two species together. The resulting conjugated species containing the linking group are also included in the invention.

Further included in the invention is the use of a quenching agent which allows direct measurement of the reaction of 2-iminothiolanes with nucleophilic groups.

6 Claims, 2 Drawing Sheets

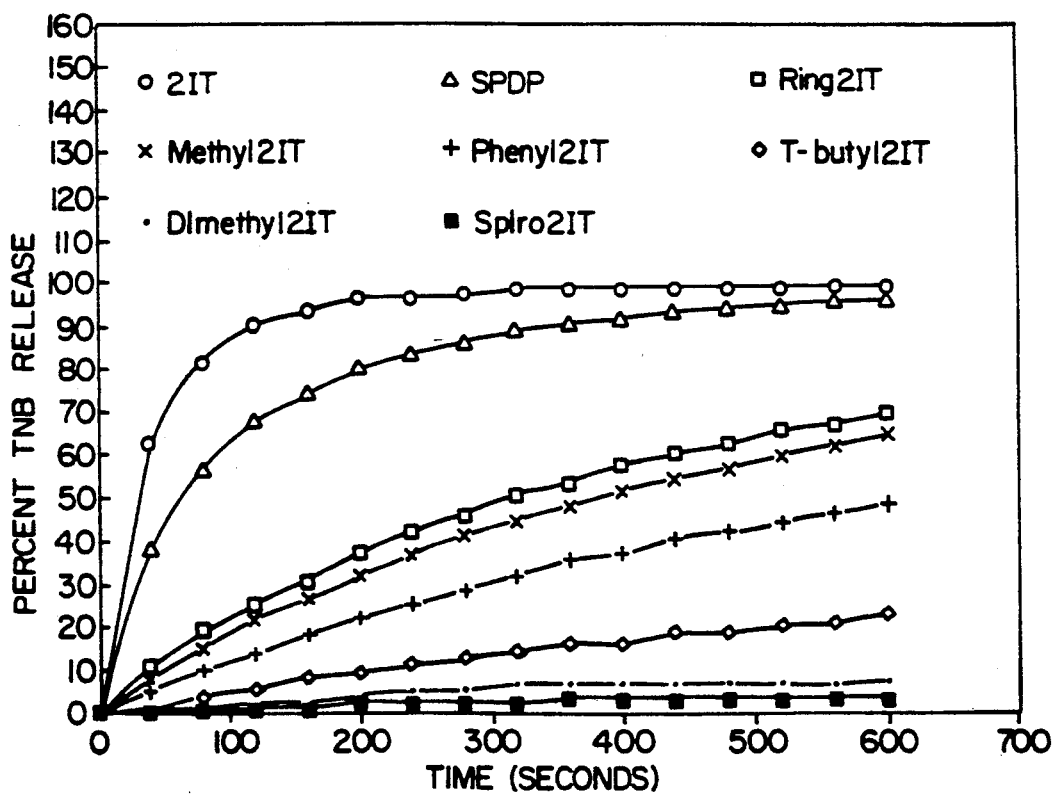
FIG._1.

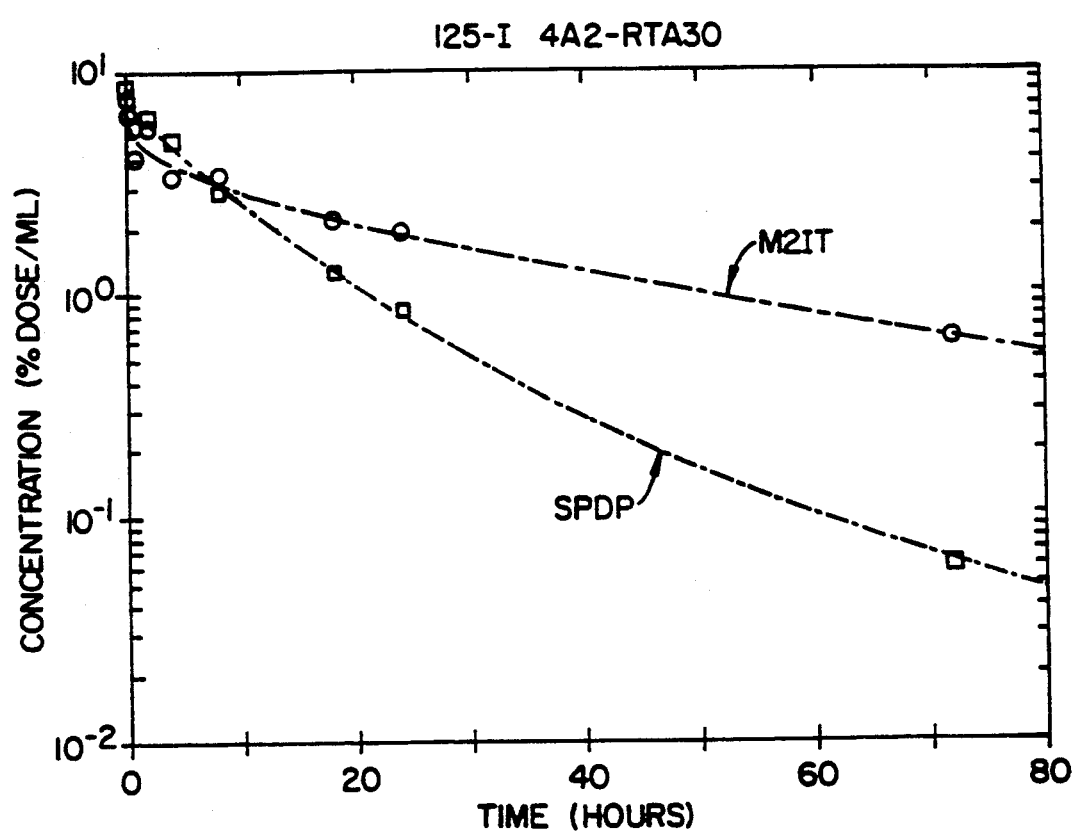
FIG._2.

HINDERED LINKING AGENTS AND METHODS

This is a division of application Ser. No. 07/454,576 now U.S. Pat. No. 5,093,475 filed Dec. 21, 1989 which is a continuation-in-part of application serial number 07/288,586 filed Dec. 22, 1988 now abandoned, which is incorporated herein by reference.

BACKGROUND OF THE INVENTION

This invention relates to the formation of conjugates, and in particular to the joining of one species to another at an amino or carbohydrate moiety utilizing a disulfide bond as part of the linkage. More particularly, it relates to substituted 2-iminothiolane hydrohalides and the use of these compounds as crosslinking agents.

The linkage of various compounds to amino or carbohydrate moieties is desirable for several reasons. In the formation of conjugates involving immunoglobulins, for example, linkage at specific regions on the immunoglobulin is often desirable for purposes of maintaining the accessibility of antigen-binding sites or of sites on the Fc chains for complement binding. The species desired for linking to amino or carbohydrate moieties often lack the ability to react directly with these moieties. Hence, some provision must be made for connecting the desired species to the compound containing the reactive moieties.

Immunotoxins are immunoglobulins chemically linked to cytotoxic agents. Generally, immunotoxins are synthesized by covalently linking cell-specific antigen-binding agents to cytotoxic agents. For example, an immunotoxin can be an immunoglobulin antibody linked to a plant or bacterial toxin, such as ricin A chain or abrin A chain. These immunotoxins bind to antigens on the target cell surface, and the cytotoxic agent then enters and kills the cell. Conjugation of the antibody and the toxin is generally by means of crosslinking agents that introduce a disulfide bond between the two proteins. Two disulfide coupling agents commonly used are N-succinimidyl-3-(2-pyridyldithio)propionate (SPDP) (Carlsson, et al., Biochem. J. 173:723-737, 1978) and 2-iminothiolane (2IT) (King, et al., Biochemistry 17:1499-1506, 1978). However, the disulfide bond formed by either of these reagents has been reported to be unstable in vivo (Thorpe, et al., Cancer Res. 47:5924-5931, 1987).

Breakdown of this disulfide linkage, with the resulting release of free antibody, is a problem since there is then less immunotoxin available to kill the target cells while at the same time the released antibody can compete with the immunotoxin for the target antigens. Thorpe et al. (supra) have synthesized two coupling agents, sodium S-4-succinimidyloxycarbonyl-α-methyl benzyl thiosulfate (SMBT) and 4-succinimidyloxycarbonyl-α-methyl-α-(2-pyridyldithio)-toluene (SMPT), which appear to have more stable disulfide linkages in vivo. However, SMBT and SMPT, as well as SPDP have low solubility in water, neutralize the positive charge on modified lysine residues, and exhibit less efficient conjugation than 2IT. Moreover, the reaction of SMBT, SMPT or SPDP with amino or carbohydrate groups cannot be monitored during modification, in contrast to the crosslinking agents of the present invention.

SUMMARY OF THE INVENTION

This invention provides novel compounds and methods for the formation of disulfide linkages. More particularly, the novel compounds are substituted 2-iminothiolane hydrohalide linking agents of the following formula (I):

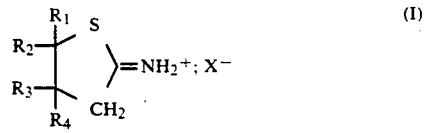

wherein,

X is halogen;

$R_1$ is $COOR_5$; halogen; nitro; unsubstituted or halogenated $C_{1-8}$alkyl; unsubstituted or halogenated $C_{1-8}$alkoxy; unsubstituted or halogenated $C_{2-8}$alkenyl; unsubstituted or halogenated $C_{2-8}$alkynyl; unsubstituted $C_{3-8}$cycloalkyl; unsubstituted aryl; aryl substituted with 1 to 3 substituents selected from halogen, amino, unsubstituted or halogenated $C_{1-8}$alkyl, or unsubstituted or halogenated $C_{1-8}$alkoxy; unsubstituted heterocycle; or heterocycle substituted with 1 to 3 substituents selected from amino, halogen, unsubstituted or halogenated $C_{1-8}$alkyl, or unsubstituted or halogenated $C_{1-8}$alkoxy;

each of $R_2$, $R_3$ and $R_4$ is independently hydrogen or selected from the values of $R_1$; or $R_1$ and $R_2$ together form a $C_{2-5}$alkylene bridge, unsubstituted or substituted with one to five $C_{1-4}$alkyl groups; or $R_1$ or $R_2$ together with $R_3$ form a $C_{1-5}$alkylene bridge, unsubstituted or substituted with one to five $C_{1-4}$alkyl groups; and $R_5$ is hydrogen or $C_{1-8}$alkyl.

Also included in the invention are methods for covalently linking two species, which methods comprise reacting one or both of the two species with a crosslinking agent of the above formula (I) and then reacting the two species together. The resulting conjugated species containing the linking group are also included in the invention.

Further included in the invention is the use of a quenching agent which allows direct measurement of the reaction of the substituted 2-iminothiolanes with nucleophilic groups and makes the reaction more efficient.

DESCRIPTION OF THE FIGURES

FIG. 1 shows the relative rates of glutathione-induced release of thionitrobenzoic acid (TNB) from the monoclonal antibody 791 conjugated with various crosslinking agents and TNB.

FIG. 2 shows the relative stabilities in rats of 4A2/5-methyl-2IT/RTA$_{30}$ and 4A2/SPDP/RTA$_{30}$ conjugates as determined by $^{125}$I radiolabelling experiments.

DETAILED DESCRIPTION OF THE INVENTION

The substituted 2-iminothiolane hydrohalides of the present invention are useful as crosslinking agents for covalently linking two proteins with a disulfide bond of controlled stability.

Some of the compounds of the invention of formula (I), specifically those where $R_1$ is lower alkyl and $R_2$-$R_4$ are hydrogen or lower alkyl, are known compounds useful as intermediates for herbicides and insecticides. These compounds are disclosed in U.S. Pat. Nos. 3,318,910 and 3,348,940. Other compounds encompassed in this invention are novel. Additionally, the use of the compounds of formula (I) as crosslinking agents is novel.

Where any of the substituents $R_1$–$R_4$ or X is or comprises halogen, such halogen is conveniently selected from bromo, chloro or fluoro.

The terms "halogenated $C_{1-8}$alkyl", "halogenated $C_{1-8}$alkoxy", "halogenated $C_{2-8}$alkenyl", and "halogenated $C_{2-8}$-alkynyl" refer to $C_{1-8}$alkyl, $C_{1-8}$-alkoxy, $C_{2-8}$alkenyl and $C_{2-8}$-alkynyl, respectively, substituted by 1 to 8, preferably 1 to 6, and more preferably 1 to 3 halogens; such halogens are preferably bromo or fluoro or a combination of the two.

The term "heterocycle" or "heterocyclic compound" refers to ring-containing compounds with 1 to 3 hetero ring atoms, which hetero atoms are selected from oxygen, sulfur or nitrogen. The heterocycle can contain one or multiple rings and the rings can be fused or unfused. Most preferably the heterocycle will contain only one ring and will be furanyl, pyranyl, thiophenyl, or pyridyl.

In the practice of the present invention, X is preferably bromo or chloro, more preferably chloro.

$R_1$ is preferably $C_{1-4}$alkyl, optionally bromo-substituted, or aryl, or together with $R_2$ forms a $C_{2-5}$alkylene bridge, or together with $R_3$ forms a $C_{1-5}$alkylene bridge.

$R_2$ is preferably hydrogen, or $C_{1-4}$alkyl, optionally bromo-substituted, or together with $R_1$ forms a $C_{2-5}$alkylene bridge.

$R_3$ is preferably hydrogen, $C_{1-4}$alkyl, or aryl, or together with $R_1$ or $R_2$ forms a $C_{1-5}$alkylene bridge optionally substituted with one to four $C_{1-2}$alkyl groups.

$R_4$ is preferably hydrogen or $C_{1-4}$alkyl.

$R_5$ is preferably hydrogen or $C_{1-4}$alkyl.

Illustrative compounds within the scope of the above formula (I) are presented in Table A.

TABLE A

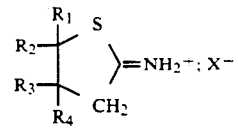

| Cpd. | $R_1$ | $R_2$ | $R_3$ | $R_4$ | X |
|---|---|---|---|---|---|
| 1 | $CH_3$ | H | H | H | Cl |
| 2 | $C_6H_5$ | H | H | H | Cl |
| 3 | $C(CH_3)_3$ | H | H | H | Cl |
| 4 | $CH_3$ | $CH_3$ | H | H | Cl |
| 5 | {—$CH_2(CH_2)_3CH_2$—} | | H | H | Cl |
| 6 | H | | {—$CH_2(CH_2)_2CH_2$—} | H | Cl |
| 7 | $CH_2CH_3$ | H | H | H | Br |
| 8 | $CH_2CH_3$ | $CH_3$ | H | H | Cl |
| 9 | {—CH—$CH_2$—CH2} | H | H | H | Cl |
| 10 | $CH_3$ | H | $CH_3$ | H | Cl |
| 11 | H | H | $CH_3$ | $CH_3$ | Cl |
| 12 | $C_6H_5$ | $CH_3$ | H | H | Cl |
| 13 | 4-$ClC_6H_4$ | H | H | H | Cl |
| 14 | 3-furanyl | H | H | H | Cl |
| 15 | $CH(CH_3)_2$ | H | H | H | Cl |
| 16 | $CH_3$ | $CH_3$ | $CH_3$ | $CH_3$ | Cl |
| 17 | $C_6H_{11}$ | H | H | H | Cl |
| 18 | $CH_2Br$ | H | H | H | Cl |
| 19 | $CF_3$ | H | H | H | Cl |
| 20 | $CH=CH_2$ | H | H | H | Cl |
| 21 | 2-$NH_2C_6H_4$ | H | H | H | Cl |
| 22 | H | {—$C(CH_3)_2$—$(CH_2)_2$—$CH_2$—} | | H | Cl |

The compounds of the present invention are prepared by conventional techniques well known among those skilled in the art, selected in accordance with the desired substituent groups. More particularly, the compounds may be prepared by the procedures set forth in U.S. Pat. Nos. 3,318,910 and 3,348,940, the disclosures of which are incorporated herein by reference. In general, a nitrile of formula (II), wherein Z is H or —C(O)$R_6$ and $R_6$ is $C_{1-6}$alkyl, is reacted with a hydrohalide H-X, such as hydrochloric acid or hydrogen chloride gas, either in an aqueous or an alcoholic medium, to give the cyclized 2-iminothiolane hydrohalide of formula (I).

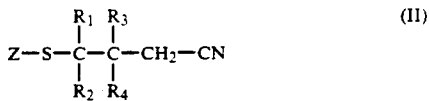

The compounds of formula (I) may be recovered from the reaction mixture in which they are formed by established procedures.

The starting materials and reagents employed in the processes for synthesizing the compounds of formula (I) are either known or, in cases where they are novel, may be produced by methods known in the art or analogous to such methods.

It will be noted that the substituted 2-iminothiolanes of the present invention have at least one chiral center. The specific compounds disclosed herein each represent a mixture of enantiomers unless otherwise indicated. The separate enantiomers as well as the mixture thereof are encompassed within the present invention.

The compounds of the present invention are useful in placing a disulfide functional group at the site of an amino or carbohydrate group on another compound, and likewise for linking two compounds at specified functional groups, i.e., an amino group on one and a thiol or nucleophilic moiety on the other.

The utility of these linking agents is in providing linkages between species in a site-specific manner with respect to at least one of the species, and often with site specificity on both species. These agents may thus be used for example in linking proteins or other molecules to amino groups or carbohydrates on other proteins. They can also be used to introduce a sulfhydryl moiety for purposes of site specificity for reaction with a nucleophilic moiety of another species.

The substituted 2-iminothiolanes of the invention exhibit UV absorbance, which absorbance is lost when the cyclic ring is opened following attack by nucleophilic compounds. Thus, these linking agents are useful because the rate and extent of hydrolysis with low molecular weight compounds (amino acids or water, for example) can be observed as the reaction takes place, enabling one to monitor and control it. The reaction may be monitored by observing with a spectrophotometer the change in absorbance at the 248 nm wavelength ($A_{248}$).

The 2-iminothiolanes of the invention also exhibit unique properties which allow direct measurement of their reaction with a protein, when the absorbance is too high at the 248 nm wavelength and cannot be read. Because the sulfur atom of the 2-iminothiolanes is cyclized into the ring structure, it is unavailable for reaction with reagents (such as aromatic disulfides) which react with sulfhydryl groups. Once ring opening occurs and a sulfhydryl becomes exposed, an aromatic disulfide (such as dithionitrobenzoic acid, DTNB) can react with the sulfhydryl. Such reaction can be monitored at discrete wavelengths (e.g., the 412 nm wavelength for DTNB, $A_{412}$). This allows direct quantitation and control of the kinetics and extent of modification, as well as the activation of sulfhydryl forms.

The crosslinking agents of the invention are water soluble, in contrast to SPDP, SMPT and SMBT. This makes them easier to use and gives better conjugation yields. Also, the ability to conduct the conjugation under aqueous conditions avoids subjecting the proteins to possible damage by organic solvents.

Linkages formed with the crosslinkers of the present invention have certain advantages over linkages formed with unsubstituted 2-iminothiolane. As shown in FIG. 1, linkages formed with the substituted 2-iminothiolanes exhibit increased stability to reduction in vitro. Additionally, the linkages of the invention should be more stable in vivo, since the presence of at least one of the groups $R_1-R_4$ should make the molecule sterically hindered towards disulfide exchange by glutathione or other thiols in serum or towards enzymatic attack which might cleave the disulfide bond prematurely.

These linking agents are particularly useful in the synthesis of immunotoxins. Immunotoxins, useful in the treatment of disease, are characterized by two components. One component is the cytotoxic agent which is fatal to a cell when absorbed. The second component, the antigen-reactive agent, provides a means for delivering the toxic agent to a particular cell type, such as T-lymphocytes or B-lymphocytes. The two components are complexed or bonded together by any of a variety of well-known chemical procedures. One of the most common and preferred methods is by using crosslinking agents with disulfide bonds. The linking agents of the present invention provide such a disulfide bond to link covalently an immunoglobulin (Ig) antigen-reactive agent, at an available amino group native to the Ig, to a sulfhydryl-containing cytotoxic agent (tox) to form an immunotoxin. Such a linkage would have the following configuration:

$$\text{Ig} - \underset{\underset{H}{|}}{N} - \overset{\overset{NH_2}{\|}}{C} - CH_2 - \underset{\underset{R_4}{|}}{\overset{\overset{R_3}{|}}{C}} - \underset{\underset{R_2}{|}}{\overset{\overset{R_1}{|}}{C}} - S - S - \text{tox}$$

When the cytotoxic agent does not contain thiol groups, such groups may be added to the toxin using substituted 2-iminothiolanes according to the methods of this invention.

In the present invention, an aromatic disulfide compound may be reacted with the immunoglobulin and the substituted 2-iminothiolane hydrohalide prior to reaction with the toxin. Examples of aromatic disulfide compounds useful in the invention are dithionitrobenzoic acid (DTNB), 2,2'- and 4,4'-di-pyridyldisulfide (DPDS), and 2,2'-dithiobis(pyridine-N-oxide). The presence of an aromatic disulfide in the immunoglobulin/2IT reaction mixture (i) allows real-time monitoring of the progress and extent of the reaction, (ii) activates the exposed sulfhydryl, and (iii) blocks reactive sulfhydryls in the immunoglobulin, preventing antibody dimerization prior to and during the subsequent reaction with the toxin.

Additionally, it has been found that both the unsubstituted and the substituted 2-iminothiolanes polymerize during the linking reaction so that a chain of two to five or more iminothiolane-derived groups often results. The presence of a quenching group such as an aromatic sulfide at the sulfhydryl of the iminothiolane linkage prevents such polymerization from occurring, resulting in a single iminothiolane-derived group at each reaction site and a more efficient reaction.

Thus, one embodiment of the present invention is a method for covalently linking two species which comprises a) reacting one or both species with either an unsubstituted or a substituted 2-iminothiolane crosslinking agent together with a quenching agent such as an aromatic disulfide, b) desalting to remove reagent, and c) mixing the two species together.

A variety of cytotoxic agents are suitable for use in immunotoxins. The cytotoxic agents contemplated by this invention can include radionuclides, such as Iodine-131, Yttrium-90, Rhenium-188, and Bismuth-212; a number of chemotherapeutic drugs, such as vindesine, methotrexate, adriamycin, and cis-platin; and cytotoxic proteins such as ribosomal inactivating proteins including abrin and ricin (or their A-chains), pokeweed antiviral protein, diphtheria toxin, pseudomonas exotoxin A, etc., or their recombinant derivatives. (See generally, "Chimeric Toxins", Olsnes and Pihl, Pharmac. Ther., 25:355-381 (1982), and "Monoclonal Antibodies for Cancer Detection and Therapy," eds. Baldwin and Byers, pp. 159-179, 224-266, Academic Press (1985), both of which are incorporated herein by reference.)

Toxin lectins are of particular interest in this invention. The cytotoxic action of toxic lectins, and especially that of ricin and abrin, has been well studied. It is known that toxic lectins consist of two polypeptide chains, A and B, linked by means of disulfide bridge(s). Cytotoxicity is associated with the A chain and its inhibition of protein synthesis in nucleated cells. The B chain is believed to be essentially a delivery vehicle for the A chain. The B chain recognizes polysaccharide units at the surface of cells and creates a high affinity interaction with such units. Once the B chain binds with polysaccharide units at the cell surface, the A chain is incorporated into the cell, blocking ribosomal protein synthesis and ultimately leading to cell death. Thus, in one embodiment of this invention, the ribosomal inactivating protein (RIP) is a toxic lectin A chain. In a further embodiment, the toxic lectin A chain is a ricin toxin A chain (RTA). The RTA may be naturally occurring or it may be a recombinant derivative thereof or it may be chemically modified, such as deglyco RTA. The use of ricin A chain is preferred in this invention.

Toxic lectins of the type of structure and function similar to ricin include abrin, modeccin and mistletoe toxin. One other category of RIPs is toxins with only one subunit having functional characteristics analogous to ricin A chain. This type of RIP lacks cytotoxicity to the intact cell because of the inherent absence of a binding fragment analogous to ricin B chain. Examples of RIPs of this latter type include gelonin and pokeweed antiviral protein.

According to the invention, any toxic lectin which may be split into A and B polypeptide chains, specifically abrin, modeccin and mistletoe toxin may be used in the same way ricin is used in the preferred embodiment. In addition, any RIP, specifically gelonin and pokeweed antiviral protein, may be used in the same way as ricin A chain. Such materials are equivalent to the toxic lectin A chain for purposes of this invention.

It is preferable in this invention to achieve cell-specific cytotoxicity by employing toxic A chains that are substantially free of lectin B chain impurities. Preferred methods for obtaining substantially pure lectin A chains are described in U.S. Pat. No. 4,590,071, which is incorporated herein by reference.

The antigen-reactive component of the immunotoxin preferably is an immunoglobulin which can be obtained from a number of sources and which is reactive with a cell-specific antigen. The term "immunoglobulin(s)" includes polyclonal antibodies, monoclonal antibodies, reactive fragments, such as Fv, Fab, F(ab$_2$), synthetic immunoglobulins and recombinant immunoglobulins, including chimeric immunoglobulins or their derivatives. Preferably, the immunoglobulins are monoclonal antibodies (mAbs) of the IgM or IgG isotype of murine, human or other mammalian origin which are reactive with most T-cells or with both T- and a subset of B-cells and, more preferably, mAbs reactive with the CD5 antigen found on both T- and B-cells.

Immunotoxins covalently bonded by the linking agent of the present invention are water soluble, have greater conjugation efficiency in comparision to SPDP or SMPT, and exhibit greatly increased stability of the disulfide bond over immunotoxins crosslinked with SPDP or 2IT.

The immunotoxins of the present invention are useful in the treatment of disease. Such immunotoxins may be applied to cells or tissue in vitro or administered to a patient in vivo in accordance with procedures well-known to those skilled in the art. The immunotoxin should be administered in a therapeutically effective dose, that is, a dose wherein the immunotoxin causes a depletion of target cells such as T-cells or B-cells such that the disease state is altered towards a more normal state. The dose of the immunotoxin preparation will vary widely, depending on the target cells, whether the administration is in vitro or in vivo, whether administration is in conjunction with other immunotoxins or therapeutic agents and other such factors.

Generally, pharmaceutical compositions containing the immunotoxins of this invention will be administered to patients in the form of "unit dosages." The term "unit dosage" refers to physically discrete units suitable as unitary dosages for human subjects and animals, each unit containing a predetermined quantity of active material designed to produce the desired pharmaceutical effect in association with the required pharmaceutical diluent, carrier, excipient or vehicle. Suitable excipients or carriers of these agents include sterile, non-pyrogenic aqueous solutions. These solutions are preferably isotonic solutions buffered in the physiological range, such as phosphate buffered saline (0.1M Na phosphate; 0.15M NaCl, pH 6.8 to 7.2). These pharmaceutical compositions may optionally include a preservative. Examples of preservatives include surfactants, particularly polysorbate 80, or the like. In addition, the preparation can be optionally lyophilized for long term storage.

Administration can be achieved by intraperitoneal injection or intravenous infusion. Intravenous administration is preferred. Dosages will vary in accordance with the size and condition of the patient. A typical unit dosage is about 5–20 mg per kilogram of body weight. A most preferred unit dosage is about 10–15 mg/kg.

The term "species" as used herein includes any compound which may be joined to a second compound at an amino or carbohydrate moiety using a disulfide bond as part of the linkage. Compounds which may be modified with the crosslinking agents of the invention generally include, but are not limited to, for example, peptides, oligopeptides and polypeptides; proteins; nucleic acids; polysaccharides; non-protein chemotherapeutic agents; carboxylic ionophores such as monensin; carbohydrate-containing molecules or resins; histochemical or immunochemical detection enzymes such as horseradish peroxidase, alkaline phosphatase, beta-galactosidase, urease, etc.; and polypeptides or proteins which recognize specific receptors or cells, such as growth factors and peptide hormones. Such compounds may be linked with each other or with other proteins such as a cytotoxic agent or an immunoglobulin. For example, histochemical or immunochemical agents may be conjugated to substituted 2-iminothiolane-modified monoclonal antibodies. Likewise, growth factors or peptide hormones, for example, may be modified by the linking agent and conjugated to a cytotoxic agent.

EXAMPLES

The following examples are presented to show the practice of the present invention and are not intended to limit the invention in any way.

The following abbreviations are used herein:
RT: room temperature.
THF: tetrahydrofuran.
PBS: phosphate-buffered saline.
DTNB: dithionitrobenzoic acid.
TNB: thionitrobenzoic acid.
IgG: immunoglobulin.
mAb: monoclonal antibody.
BP: base peak.
b.p.: boiling point, in degrees Celsius.
m.p.: melting point, in degrees Celsius.

NMR: nuclear magnetic resonance at 60 MHz; all chemical shifts are given in δ ppm values relative to tetramethylsilane (TMS).

LRMS low resolution mass spectrum.

IR: infrared spectra; values given in cm$^{-1}$. s.32 strong, br.=broad, v.s.=very strong, v.br.=very broad.

IL2: interleukin 2.

IND1 is a monoclonal antibody of isotype IgG2a, produced by cell line XMMME-001, deposited with the ATCC, accession no. HB 8759. The mAb is described in U.S. Pat. No. 4,590,071.

IND2 is a monoclonal antibody of isotype IgG2a, produced by cell line XMMME-002, deposited with the ATCC, accession no. HB 8760. The mAb is described in U.S. Pat. No. 4,590,071.

791 is a monoclonal antibody of isotype IgG2b, produced by cell line XMMCO-791, deposited with the ATCC, accession no. HB 9173. The mAb is described in U.S. Pat. No. 4,708,862.

4A2 (also known as 4A) is a monoclonal antibody of isotype IgG2a. The hybridoma cell line producing 4A2 is on deposit with the ATCC, accession no. HB 8350. The mAb is described in U.S. Pat. No. 4,677,056.

H65 is a monoclonal antibody of isotype IgG1 and is produced by hybridoma cell line XMMLY-H65, deposited with the ATCC and given the accession no. HB 9286. The antibody is prepared as described in Kernan et al., J. Immunol. 133:137 (1984).

RTA$_{30}$ is a species of ricin toxin A chain (RTA) having a molecular weight of approximately 30 kD, such as described in detail by Fulton et al., J. Biol. Chem. 281:5314–5319 (1986) and Vidal et al., Int. J. Cancer 36:705–711 (1985).

A. PREPARATION OF SUBSTITUTED 2-IMINOTHIOLANE HYDROHALIDES

EXAMPLE 1

5-Methyl-2-iminothiolane hydrochloride (Methyl-2IT)

4-Thioacetylpentanenitrile (7.2 g) was dissolved in dry methanol (50 mL), and hydrogen chloride gas was bubbled into the solution for 5 min. at RT. The reaction mixture was stirred for 20 hr. at RT, and then was concentrated in vacuo until white solid began to precipitate out. Ether was added and a small amount of solid product was filtered off. The filtrate was concentrated to give an orange oil, which was slurried with ethyl acetate. Ethanol was then added at 50° C. until a solution was obtained, after which the mixture was cooled to −20° C. and ether was added. Further cooling gave 5-methyl-2-iminothiolane hydrochloride as pale pink needles, 4.16 g (60%), m.p. 122°–123° C. (compound 1, Table A). The molecular structure of the product was confirmed as that of the title compound by NMR and IR as follows.

NMR (DMSO): 4.10 (m,1H, methine), 3.23 (ps.t, 2H), 1.60–2.67 (m, 2H), 1.38 (d, 2H, J=7.0, 5-Me).

IR (KBr): 2810 (v.s., v. br.), 1615 (s., br., C=N), 1530, 1450, 1415, 1240, 1030, 990, 890 (s., br.), 685 (s., C-S), 425.

EXAMPLE 2

5-Phenyl-2-iminothiolane hydrochloride (Phenyl-2IT)

4-Phenyl-4-thioacetylbutanenitrile (2.82 g) was dissolved in dry methanol (30 mL), and hydrogen chloride gas was bubbled into the solution for 5 min. at RT, followed by stirring at RT for 4 hr. The reaction mixture was concentrated in vacuo, then dissolved in a mixture of ethanol/ethyl acetate at 50° C. After cooling several hours at −20° C., ether was added to precipitate a white solid, which was filtered off and dried in vacuo to give 5-phenyl-2-iminothiolane hydrochloride, 1.22 g (44%), m.p. 142°–144° C. (compound 2, Table A) The molecular structure of the product was confirmed as that of the title compound by NMR and IR as follows.

NMR (DMSO): 7.50 (br.s, 5H, phenyl), 5.40 (dd, 1H, methine), 3.25–3.75 (m, 2H), 2.20–2.84 (m, 2H).

IR (KBr): 3360, 2870 (v.s., v.br.), 1615 (s., br., C=N), 1515, 1495, 1450, 1405, 1325, 1020, 985, 830, 770, 760, 700 (s.), 675 (s.).

EXAMPLE 3

5-t-Butyl-2-iminothiolane hydrochloride (t-Butyl-2IT)

5,5-Dimethyl-4-mercaptohexanenitrile (1.55 g) was dissolved in dry methanol (15 mL) and HCl gas was bubbled into the solution for 5 min., after which the solution was stirred at RT for 2 hr. Additional HCl gas was bubbled into the solution and stirring continued for another hour. The reaction mixture was concentrated in vacuo. The resulting oil was triturated with warm ethyl acetate, and then warm ethanol was added until a solution was obtained. The mixture was cooled to −20° C. and ether was added. The mixture was cooled overnight, then filtered to give 5-t-butyl-2-iminothiolane hydrochloride as a white solid, 0.42 g (22%), m.p. 226°–228° C. (compound 3, Table A). The molecular structure of the product was confirmed as that of the title compound by NMR and IR as follows.

NMR (DMSO): 4.10 (dd, 1H, methine), 3.25 (m, 2H), 1.86–2.70 (m, 2H), 1.03 (s, 9H, t-Bu).

IR (KBr): 2890 (v.s., v.br.), 1620 (s., br., C=N), 1400 (s.), 1370, 1255, 1175, 995, 690 (s., C-S).

EXAMPLE 4

5,5-Dimethyl-2-iminothiolane hydrochloride (Dimethyl-2IT)

Following the procedures of Examples 1 and 2, HCl gas was bubbled through a solution of 4-mercapto-4-methylpentanenitrile (3.6 g) in dry methanol. The crude product was worked up to give 5,5-dimethyl-2-iminothiolane hydrochloride as a white solid, 3.0 g (65%), m.p. 156°–159° C. (compound 4, Table A). The molecular structure of the product was confirmed as that of the title compound by NMR and IR as follows.

NMR (DMSO): 3.45 (t, 2H, J=7.0), 2.18 (t, 2H, J=7.0), 1.60 (s, 6H, 2-Me).

IR (KBr): 2900 (v.s., v.br), 1610 (s, br, C=N), 1510, 1325, 1240, 1215, 1120, 990, 875, 845, 690 (s, C-S).

EXAMPLE 5

2-Imino-1-thiaspiro[4.5]decane hydrochloride (Spiro-2IT)

To a solution of n-butyllithium (0.67 mL of 10M solution in hexanes) in THF (10 mL) at −78° C. under argon was added acetonitrile (0.35 mL, 0.67 mmol). The mixture was stirred for 10 min., after which 1-thiaspiro[2.5]octane (0.86 g, 0.67 mmol) in dry THF (2 mL) was added. The cooling bath was removed and the reaction was stirred for 2 hr. After quenching with a mixture of conc. HCl (1.5 mL) and water (3.5 mL), the layers were separated and the aqueous phase was extracted with ethyl acetate (2×25 mL). The combined organic layers were dried over sodium sulfate and concentrated in vacuo to give an oil. The oil was dissolved in methanol (10 mL) and bubbled vigorously with HCl gas for 5 min. The mixture was then stirred overnight at RT. The solvent was removed in vacuo and the oily residue was triturated with ether until a solid was obtained, to give 2-imino-1-thiaspiro[4.5]decane hydrochloride, 0.17 g, m.p. 130°–135° C. (compound 5, Table A). The molecular structure of the product was confirmed as that of the title compound by NMR and IR as follows.

NMR (DMSO): 8.23, 7.38, 6.53 (3 br s, each integrates to ca. 0.5H, all completely exchanged with D20, NH's), 3.36 (t, J=7.0, 2H, 3-CH2), 2.18 (t, J=7.0, 2H, 4-CH2), 1.00-2.00 (br m, 10H, cyclohexyl).

IR (KBr): 3500–2500 (v.s., v.br.), 1610 (s., br.), 1525, 1445 (s.), 1405 (s), 1250, 1205, 1130 1100 1020, 990, 875 (s.), 690 (s.), 445.

EXAMPLE 6

2-Imino-1-thiabicyclo[3.4.0]nonane hydrochloride (Ring-2IT)

Under argon, THF (30 mL) was cooled to −78° C., after which n-butyllithium (10M in hexanes, 3.59 mL) was added dropwise, followed by acetonitrile (1.88 mL, 35.9 mmol). The reaction mixture was stirred for 10 min. at −78° C., then cyclohexene sulfide (3.90 g, 34.2 mmol) in THF (10 mL) was added dropwise. After addition was complete, the cooling bath was removed and the mixture was allowed to warm to RT. After 2 hrs., the reaction was re-cooled and quenched by addition of a mixture of conc. HCl (6 mL) and water (15 mL). The layers were separated and the aqueous layer was rinsed with ethyl acetate (2×25 mL). The combined organic layers were dried over $Na_2SO_4$ and concentrated in vacuo to give a crude brown liquid (5.08 g). The crude product was distilled in vacuo to give a colorless liquid, 2.26 g, b.p. 85°–89° C. (0.3 mm), with the following NMR, IR and LRMS.

NMR (CDCl3): 2.68 (d, 2H, CH2CN), 2.32 (s, 1H), 1.0–2.30 (m, 10H, cyclohexyl).

IR (neat on NaCl): 2930 (s.), 2860 (s.), 2530 (w., SH), 2250 (m., CN), 1730, 1450 (s.), 1425, 1195, 965.

LRMS (m/e, %BP): 155 (M+, 29.9).

The above liquid was dissolved in dry methanol (30 mL) and HCl gas was bubbled vigorously into the solution for 5 min., after which the reaction mixture was stirred overnight at RT. Concentration in vacuo gave a white solid, which was slurried in ethyl acetate and treated with hot ethanol until a solution was obtained. Cooling to −20° C. gave a white crystalline solid which was filtered off and dried in vacuo to give 2-imino-1-thiabicyclo[3.4.0]nonane hydrochloride, 3.13 g (59%), m.p. 249° C. (dec.) (compound 6, Table A). The molecular structure of the product was confirmed as that of the title compound by NMR and IR as follows.

NMR (400 mHz, DMSO): 3.57 (dt, J=11.5, 3.4, 1H, H-8), 3.24 (dd, J=17, 5.7, 1H, H-3), 2.91 (dd, J=17, 1H, H-3'), 2.22 (dd, 1H, H-9), 1.94–2.03 (m, 2H), 1.75–1.84 (m, 2H), 1.45–1.54 (m, 1H), 1.28–1.39 (m, 3H).

IR (KBr): 2840 (v.s., v.br.), 1624 (s., C=N), 1528, 1450, 998, 895, 880, 694 (s.).

B. PREPARATION OF CONJUGATED IMMUNOTOXINS

EXAMPLE 7

IND1/5-methyl-2IT/RTA30 toxin

A mixture of IND1 mAb (20.0 mM, 3.0 mg/mL), DTNB (0.5 mM), and 5-methyl-2-iminothiolane hydrochloride (3.4 mM) in PBS (pH 7.0) was incubated at 25° C. until the $A_{412}$=0.51 (ca. 1.8 SH/mol). The reaction mixture was then desalted on a column of Sephadex G25Fine resin (G25F; Pharmacia) equilibrated with PBS. The TNB:protein ratio was measured, indicating 2.0:1.

The above IND1/5-methyl-2IT/TNB complex (6.4 μM) was mixed with RTA30 (33.0 μM), and the mixture was incubated at 4° C. for 16 hr. The reaction mixture was purified to give the immunotoxin IND1/5-methyl-2IT/RTA30.

EXAMPLE 8

791/5-methyl-2IT/RTA30 toxin

A mixture of 791 mAb (30.0 μM, 4.5 mg/mL), DTNB (2.0 mM), and 5-methyl-2-iminothiolane hydrochloride (3.0 mM) in PBS (pH 7.0) was incubated at 25° C. until the $A_{412}$=0.60 (ca. 1.2 SH/mol). The reaction mixture was then desalted on G25F and the TNB:protein ratio was measured, indicating 1.1:1.

The above 791/5-methyl-2IT/TNB complex (11.0 μM) was mixed with RTA30 (44.0 μM). The mixture was incubated at RT for 15 min., and then at 4° C. for 16 hr. The reaction mixture was purified to give the immunotoxin 791/5-methyl-2IT/RTA30.

EXAMPLE 9

791/5-phenyl-2IT/RTA30 toxin

A mixture of 791 mAb (47.0 μM, 7.0 mg/mL), DTNB (3.0 mM), and 5-phenyl-2-iminothiolane hydrochloride (2.0 mM) in PBS (pH 7.0) was incubated at 25° C. until the $A_{412}$=1.10 (ca. 1.6 SH/mol). The reaction mixture was then desalted on G25F and the TNB:protein ratio was measured, indicating 1.7:1.

The above 791/5-phenyl-2IT/TNB complex (7.3 μM) was mixed with RTA30 (44.0 μM). The mixture was incubated at RT for 15 min., and then at 4° C. for 16 hr. The reaction mixture was purified to give the immunotoxin 791/5-phenyl-2IT/RTA30.

EXAMPLE 10

H65/5-methyl-2IT/RTA30 toxin

Following the above procedures, H65 mAb is reacted with 5-methyl-2-iminothiolane hydrochloride and DTNB, and the resulting complex is reacted with RTA30 to give the immunotoxin H65/5-methyl-2IT/RTA30.

EXAMPLE 11

IL2/5-methyl-2IT/RTA30 toxin

A mixture of IL2, DTNB and 5-methyl-2-iminothiolane hydrochloride is incubated on ice for 4 hr. It is then desalted on G25F equilibrated in 25 mM borate and 50 mM NaCl, pH 8.5, and the TNB:protein ratio is measured, giving 1.0:1.

The above IL2/5-methyl-2IT/TNB complex is mixed with RTA30 and the mixture is incubated at 4° C. for 16 hr. to give IL2/5-methyl-2IT/RTA30.

EXAMPLE 12

4A2/5-methyl-2IT/RTA$_{30}$ toxin - Controlled conjugation

Following the procedures of Examples 7-10, 4A2 mAb is reacted with 5-methyl-2-iminothiolane hydrochloride and DTNB and then desalted to give 4A2/5-methyl-2IT/TNB complex, with a TNB:mAb ratio of 4.7:1.

The above complex (1.1 mg/mL, 7.3 μM) is mixed with RTA$_{30}$ (1.4 mg/mL, 47.0 μM), and the mixture is incubated at RT while the A$_{412}$ is monitored. When the $A_{412}$ is 0.185 (ca. 1.8 RTA/mAb), 2-mercaptoethylamine (50 μM) is added. The $A_{412}$ is again monitored, and when the reading reaches the maximum (0.47, 33 μM=96%), the product is chromatographed on a column of agarose and acrylamide mix resin (AcA44; LKB Pharmacia) equilibrated in PBS, pH 7.5, to give 4A2/5-methyl-2IT/$RTA_{30}$ with an analysis (on gel) of 1.9 RTA/mAb.

EXAMPLE 13

IND1/5-methyl-2IT/$RTA_{30}$ toxin - Controlled conjugation

Following the procedures of Example 7, IND1/5-methyl-2IT/TNB complex is prepared, with a TNB:mAb ratio of 5.1:1.

The above complex (6.7 μM) is mixed with $RTA_{30}$ (1.4 mg/mL, 47.0 μM), and the mixture is incubated at RT while the $A_{412}$ is monitored. When the $A_{412}$ is 0.105 (ca. 1.1 RTA/mAb), cysteine is added (265 μM, 5x RTA). The $A_{412}$ is monitored, and when the reading reaches a plateau (0.48, 98% maximal TNB ) the product is purified to give IND1/5-methyl-2IT/$RTA_{30}$ with an analysis (on gel) of 1.14 RTA/mAb.

EXAMPLE 14

791/5-t-butyl-2IT/$RTA_{30}$ toxin

A mixture of 791 mAb (20 μM, 3 mg/ml), DTNB (2.5 mM) and 5-t-butyl-2IT (0.5 mM) in 0.1M sodium phosphate, 0.1M sodium chloride, pH 7.5, was incubated at 26° C. until the absorbance at 412 nm reached 0.4 (ca. 1.4 SH/mol mAb). The reaction mixture was then desalted by chromatography on a column of Sephadex G25Fine equilibrated in PBS containing 0.5 mM EDTA, pH 7.0. The TNB:mAb ratio, as measured by reaction with DTT, was 1.3:1.

The above 791/5-t-butyl-2IT/TNB complex (1.0 mg/ml, 6.7 μM) and $RTA_{30}$ (2.0 mg/ml, 67 μM, a five-fold molar excess) were mixed together and incubated at 4° C. for 16 hr. The reaction mixture was purified to give the immunotoxin 791/5-t-butyl-2IT/$RTA_{30}$, which contained 0.8 RTA/mAb.

EXAMPLE 15

7915-t-butyl-2IT/$RTA_{30}$ toxin

Following the procedure of Example 14, 791 mAb was reacted with 5-t-butyl-2IT in the presence of the aromatic disulfide dithiobis(pyridine-N-oxide). The reaction was monitored at 332 nm and terminated when the $A_{332}$=0.125 (ca. 1.5 SH/mol mAb). The resultant 791/5-t-butyl-2IT/thiopyridine-N-oxide had a thiopyridine-N-oxide:mAb ratio of 1.4:1. Reaction with a five-fold molar excess of $RTA_{30}$ yielded 791/5-t-butyl-2IT/$RTA_{30}$ containing an RTA/mAb ratio of 1.3:1.

EXAMPLE 16

H65/2IT/$RTA_{30}$ toxin

A mixture of H65 mAb (3 mg/ml, 20 μM) and 2-iminothiolane hydrochloride (300 μM) in 0.1M sodium phosphate, 0.1M sodium chloride, pH 7.5, were incubated at 37° C. for 2 hr. The reaction was quenched by the addition of glycine to 50 mM, and the derivatized mAb was purified by chromatography on a column of Sephadex G25Fine equilibrated in PBS containing 1 mM EDTA, pH 7.2. The free SH/mAb ratio, as measured by the addition of DTNB, was 1.5:1.

The H65/2IT-SH complex prepared above was mixed with $RTA_{30}$ which had been previously derivatized with DTNB (making $RTA_{30}$-TNB) such that the final concentration of each reagent was 2.0 mg/ml (13 μM and 67 μM, respectively). The mixture was incubated for 2 hr. at 25° C. and then an additional 35 hr. at 4° C., followed by purification of the H65/2IT/$RTA_{30}$ conjugate. The RTA/mAb ratio was 0.6:1.

C. COMPARATIVE DATA

EXAMPLE 17

Comparison of efficiencies of conjugation with substituted 2-IT

Samples of 791/5-methyl-2IT/TNB complex (from Example 8) and 791/5-phenyl-2IT/TNB complex (from Example 9) were mixed with 4.0- and 6.3-fold molar excess, respectively, of RTA. Conjugation was allowed to proceed as in Examples 7–10. After conjugation was complete, aliquots were analyzed by SDS-PAGE and densitometry of stained bonds. Percent substitution was determined by dividing the RTA/mAb ratio of the product by the TNB/mAb ratio of the modified antibody. The results are presented in Table B.

For these samples, substitution efficiency was 47% and 82% for mixtures containing 4- and 6-fold molar excess of RTA. In contrast, for SPDP-modified 791, a 10-fold molar ratio of RTA/mAb yielded 40–50% substitution. Thus, less RTA can be used for conjugate construction with the 2-iminothiolane derivatives.

TABLE B

| Sample | TNB/mAb ratio | RTA/mAb ratio | | % Subst. |
|---|---|---|---|---|
| | | Mixture | Product | |
| 5-methyl-21T | 1.1 | 4.0 | 0.9 | 82 |
| 5-phenyl-21T | 1.7 | 6.3 | 0.8 | 47 |

EXAMPLE 18

Comparison of conjugation efficiencies with alternate aromatic disulfides

A comparison of the data from Examples 14 and 15 illustrate that 791 mAb derivatized with dithiobis(pyridine-N-oxide) produced a more effective leaving group than 791 mAb derivatized with DTNB. Although the modification ratios (activated SH/mAb) were very similar (1.3–1.4), under identical conditions 62% of the leaving groups present on 791/TNB were replaced as compared to 93% of those present on 791/thiopyridine-N-oxide. Conjugation efficiencies can therefore be further enhanced by appropriate selection of the aromatic disulfide.

EXAMPLE 19

Properties and stability of substituted 2-iminothiolanes compared with unsubstituted 2-iminothiolane and SPDP Tables C and D present properties for representative substituted 2-iminothiolanes as well as for the unsubstituted iminothiolane and for SPDP.

Table C gives the reaction rates of the various compounds. The following reaction rates were measured:

a. The rate of hydrolysis of the 2-iminothiolane rings in PBS (pH 7.2), monitored at 248 nm.

b. The rate of reaction of the 2-iminothiolanes with 160 mM glycine in PBS (pH 7.2), monitored by coupling the reaction with 0.5 mM DTNB and following the change in absorbance at 412 nm.

c. The rate of reaction of the 2-iminothiolanes (0.5 mM) with 791 mAb (20 μM), as monitored by coupling the reaction with 2.5 mM DTNB in 0.1M NaPO4, 0.1M NaCl, pH 7.5, and monitoring the change in absorbance at 412 nm.

d. The initial rate of TNB release from 791/iminothiolane/TNB induced by glutathione. Samples contained ca. 10 μM of protein-S-S-TNB and 200 μM of glutathione in PBS containing 0.5 mM EDTA, pH 7.25, and were monitored at 412 nm. FIG. 1 presents the results graphically.

TABLE C

| Cpd. | lambda max. | E 1 mM 248 nm | Hydrolysis (%/hr) | Glycine $k \times 10^3$ $(s^{-1})$ | 791 $k \times 10^5$ $(s^{-1})$ | TNB $k \times 10^5$ $(s^{-1})$ |
|---|---|---|---|---|---|---|
| 2IT | 247 | 8.72 | 10.2 | 5.3 | 5.0 | 942.0 |
| ring-2IT (Ex. 6) | 250 | 9.07 | 13.4 | 3.4 | 5.6 | 82.1 |
| methyl-2IT (Ex. 1) | 247 | 9.27 | 5.4 | 4.8 | 4.0 | 75.3 |
| phenyl-2IT (Ex. 2) | 246 | 9.00 | 1.5 | 5.2 | 8.8 | 45.8 |
| t-butyl-2IT (Ex. 3) | 248 | 11.7 | 6.1 | 4.4 | 7.4 | 16.4 |
| dimethyl-2IT (Ex. 4) | 247 | 10.8 | 6.9 | 3.5 | 4.6 | 0.13 |
| spiro-2IT (Ex. 5) | 248 | 10.7 | 5.6 | 3.0 | 4.6 | 0.11 |
| SPDP | — | — | — | — | — | 262.0 |

The relative increase in disulfide stability (or, the relative rate reduction) of the substituted 2-iminothiolanes compared to unsubstituted 2-iminothiolane and to SPDP is presented in Table D. It was measured by dividing the rate constant for unsubstituted 2-iminothiolane ($9.42 \times 10^{-3}$) by that for each of the substituted 2-iminothiolanes. The relative increase in disulfide stability was also compared to 791/SPDP/TNB, and was determined as for 2IT.

791/SPDP/TNB was prepared by derivatizing 791 mAb with SPDP following conventional procedures and conditions, removing any byproducts by gel filtration, releasing the PDP group with 1 mM DTT, and then reacting the liberated sulfhydryl with DTNB. Following gel filtration, the rate of TNB release was measured as in Example 19d above.

TABLE D

| | Increase in Disulfide Stability Relative to: | |
|---|---|---|
| Cpd. | 2IT | SPDP |
| 2IT | 1.0 | 0.3 |
| ring-2IT (Ex. 6) | 11.5 | 3.2 |
| methyl-2IT (Ex. 1) | 12.5 | 3.5 |
| phenyl-2IT (Ex. 2) | 20.6 | 5.8 |
| t-butyl-2IT (Ex. 3) | 57.4 | 16.2 |
| dimethyl-2IT (Ex. 4) | 7246.0 | 2046.0 |
| spiro-2IT (Ex. 5) | 8564.0 | 2418.0 |
| SPDP | 3.6 | 1.0 |

EXAMPLE 20

Preparation and in vitro stability of immunoconjugates

Immunoconjugates were prepared from the activated 791/iminothiolane/TNB derivatives, as described in Examples 8, 9, 14, and 15, by reaction with RTA30 at RT for 3 h followed by an additional 16 h at 4° C. (no conjugates were made with spiro-2IT or dimethyl-2IT). Residual free RTA30 was removed by size-exlusion chromatography on AcA44 resin equilibrated in 0.1M NaPO4, 0.1M NaCl, pH 7.5 at 4° C. The relative stability of these and other conjugates was evaluated by quantitating the amount of RTA30 released following incubation with increasing concentrations of glutathione. The concentration of glutathione that produced 50% release of the RTA30 (relative to samples incubated with 10 mM 2-mercaptoethanol) was termed the RC50, providing a means to compare the stability of the different conjugates. Table E shows the results of such a comparison, where the relative stability of each conjugate has been normalized to that of 791/SPDP/RTA30. The methyl-2IT immunoconjugate was roughly 8-times more stable than the corresponding SPDP conjugate, followed by phenyl-2IT (5.2 fold) and ring-2IT (3.7 fold). Similar results were obtained with 4A2 antibody.

Cytotoxicity - Each conjugate was also tested for its ability to inhibit protein synthesis in antigen-bearing target cells in a standard assay. 791T/M cells were incubated with 791 immunoconjugates at concentrations ranging between 2 and 2000 ng/ml for 68 h at 37° C. Following a 4 h pulse with $^3$H-leucine, the amount of cell-associated radioactivity was quantified. The concentration of immunoconjugate that inhibited protein synthesis by 50% (relative to untreated controls) is termed the IC$_{50}$. Table E presents the results, which indicate that the enhanced stability of the iminothiolane-linked conjugates did not adversely affect cytotoxicity. For reference, the activity of an SMCC-linked conjugate (which produces a non-reducible thioether linkage) is also shown.

EXAMPLE 21

Preparation and in vivo stability of immunoconjugates

The stabilities of the 4A2/methyl-2IT/RTA$_{30}$ and 4A2/SPDP/RTA$_{30}$ immunotoxins were further examined in animals. Samples of each conjugate were prepared with the 4A2 antibody (following the method of Example 12), and then radiolabelled with $^{125}$I to ca. 1 μCi/μg by the iodogen method, *Biophys. Res. Comm.* (1978) 80:849–857 (see U.S. Pat. No. 4,708,862). Aliquots of solution containing the immunoconjugates were injected intravenously into rats. Blood samples were periodically removed from the rats and the amount of radioactivity in the serum was determined. The serum counts represent not only intact conjugate, but also the fraction of conjugate that has lost the RTA$_{30}$ portion by deconjugation. (Free RTA$_{30}$ is cleared quickly and does not contribute to the total serum radioactivity.) Therefore, in order to determine the percentage of intact conjugate at each time point, serum aliquots were also analyzed by SDS-PAGE and autoradiography. These data were then used to create corrected conjugate clearance profiles. The results presented in FIG. 2, indicate that the methyl-2IT-linked conjugate was roughly 3-fold more stable in rats than the SPDP conjugate, as measured by the mean residence times (41.3 and 14.3 hours, respectively).

TABLE E

Stability and cytotoxicity of 791 immunotoxins

| Sample | Stability$^a$ Relative to 791/SPDP/RTA$_{30}$ | IC$_{50}$$^b$ (ng/ml) |
|---|---|---|
| 791/SPDP/RTA$_{30}$ | 1.0 | 11.4 |
| 791/21T/RTA$_{30}$ | 0.6 | 9.6 |
| 791/ring-2IT/RTA$_{30}$ | 3.7 | 9.8 |
| 791/methyl-21T/RTA$_{30}$ | 8.3 | 10.8 |
| 791/phenyl-21T/RTA$_{30}$ | 5.2 | 16.2 |
| 791/tert-butyl-21T/RTA$_{30}$ | 3.0 | 7.2 |
| 791/SMCC/RTA$_{30}$ (thioether) | nd. | 1412.0 |

$^a$Ratios of the glutathione concentration that releases 50% of the conjugated RTA$_{30}$ (the RC$_{50}$) relative to the RC$_{50}$ for 791/SPDP/RTA$_{30}$.
$^b$The concentration of each immunotoxin that inhibits protein synthesis in antigen-bearing 791T/M cells by 50% in the standard 72 h assay.

What is claimed is:

1. A compound of the following formula (I):

$$R_2 - \overset{R_1}{\underset{R_4}{\overset{|}{C}}} - \overset{S}{\underset{CH_2}{\overset{|}{C}}} = NH_2^+; X^- \quad (I)$$

wherein,

X is halogen;

R$_1$ is COOR$_5$; halogen; nitro; halogenated C$_{1-8}$alkyl; unsubstituted C$_{1-8}$alkoxy; halogenated C$_{1-8}$alkoxy; unsubstituted C$_{2-8}$alkenyl; halogenated C$_{2-8}$alkenyl; unsubstituted C$_{2-8}$alkynyl; halogenated C$_{2-8}$alkynyl; unsubstituted C$_{3-8}$cycloalkyl; unsubstituted aryl; aryl substituted with 1 to 3 substituents selected from halogen, amino, unsubstituted or halogenated C$_{1-8}$alkyl, or unsubstituted or halogenated C$_{1-8}$alkoxy; unsubstituted heterocycle; or heterocycle substituted with 1 to 3 substituents selected from halogen, amino, unsubstituted or halogenated C$_{1-8}$alkyl, or unsubstituted or halogenated C$_{1-8}$alkoxy;

each of R$_2$, R$_3$ and R$_4$ is independently hydrogen or selected from the values of R$_1$; or R$_1$ and R$_2$ together form a C$_{2-5}$alkylene bridge, unsubstituted or substituted with one to five C$_{1-4}$alkyl groups; or R$_1$ or R$_2$ together with R$_3$ form a C$_{1-5}$alkylene bridge, unsubstituted or substituted with one to five C$_{1-4}$alkyl groups; and R$_5$ is hydrogen or C$_{1-8}$alkyl.

2. A compound according to claim 1 wherein R$_1$ is C$_{3-6}$cycloalkyl or phenyl.

3. A compound according to claim 2 wherein each of R$_3$ and R$_4$ is hydrogen.

4. A compound according to claim 2 wherein each of R$_2$, R$_3$ and R$_4$ is hydrogen.

5. A compound according to claim 1 wherein R$_1$ and R$_2$ together form a C$_{2-5}$alkylene bridge and each of R$_3$ and R$_4$ is hydrogen.

6. A compound according to claim 1 wherein R$_1$ and R$_3$ together form a C$_{1-5}$alkylene bridge and each of R$_2$ and R$_4$ is hydrogen.

* * * * *